United States Patent
Yui et al.

(10) Patent No.: US 10,395,766 B2
(45) Date of Patent: Aug. 27, 2019

(54) DIAGNOSTIC PROCESS ANALYSIS SYSTEM

(71) Applicant: HITACHI, LTD., Tokyo (JP)

(72) Inventors: Syuntaro Yui, Tokyo (JP); Kunihiko Kido, Tokyo (JP); Kazuyuki Shimada, Tokyo (JP); Masayuki Ohta, Tokyo (JP); Jumpei Sato, Tokyo (JP); Toru Hisamitsu, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 774 days.

(21) Appl. No.: 14/376,629

(22) PCT Filed: Jun. 28, 2013

(86) PCT No.: PCT/JP2013/067759
§ 371 (c)(1),
(2) Date: Aug. 5, 2014

(87) PCT Pub. No.: WO2014/196087
PCT Pub. Date: Dec. 11, 2014

(65) Prior Publication Data
US 2015/0278459 A1  Oct. 1, 2015

(51) Int. Cl.
*G06F 19/00* (2018.01)
*G16H 40/20* (2018.01)
(Continued)

(52) U.S. Cl.
CPC ........ *G16H 40/20* (2018.01); *G06Q 10/063* (2013.01); *G06Q 50/22* (2013.01); *G16H 50/70* (2018.01)

(58) Field of Classification Search
USPC ........................................ 705/2–4
See application file for complete search history.

(56) References Cited

U.S. PATENT DOCUMENTS 8,538,906 B2 * 9/2013 Ridgeway ............ G06F 19/345
706/50
2003/0046110 A1 * 3/2003 Gogolak .................. G06F 19/24
705/2
(Continued)

FOREIGN PATENT DOCUMENTS

JP  2003-331055 A  11/2003
JP  2005-202547 A  7/2005
(Continued)

OTHER PUBLICATIONS

Viganò, Antonio, et al. "Survival prediction in terminal cancer patients: a systematic review of the medical literature." Palliative Medicine 14.5 (2000): 363-374.*
(Continued)

*Primary Examiner* — Mark Holcomb
(74) *Attorney, Agent, or Firm* — Mattingly & Malur, PC

(57) ABSTRACT

Upon evaluation of a value of a diagnostic process, the value of a diagnostic process is evaluated not based on a simple cost but on a cost required for all processes of a patient who was in the diagnostic process through a follow-up survey. Diagnostic processes that are not relevant to a target diagnostic process are eliminated, clustering is performed on patients to divide the patients into clinically meaningful homogeneous groups, and the target diagnostic process is evaluated for each of the homogeneous groups. For the purpose, importance scores of data pieces of the clinical data are calculated and the relevant data is output using the output result of the medical knowledge extraction unit, clustering is performed on patients in the clinical data, and a clinical index and a cost are output for each of the clusters.

20 Claims, 18 Drawing Sheets

(51) Int. Cl.
*G06Q 50/22* (2018.01)
*G06Q 10/06* (2012.01)
*G16H 50/70* (2018.01)

(56) References Cited

U.S. PATENT DOCUMENTS

| | | | |
|---|---|---|---|
| 2003/0216939 A1 | 11/2003 | Bito et al. | |
| 2005/0261941 A1* | 11/2005 | Scarlat | G06Q 50/24 705/3 |
| 2008/0172251 A1 | 7/2008 | Reichert et al. | |
| 2014/0052475 A1* | 2/2014 | Madan | G06F 19/3437 705/3 |
| 2014/0100884 A1* | 4/2014 | Hamilton | G06F 19/327 705/3 |

FOREIGN PATENT DOCUMENTS

| | | |
|---|---|---|
| JP | 2008-047154 A | 2/2008 |
| JP | 2010-191891 A | 9/2010 |
| JP | 2011-243140 A | 12/2011 |

OTHER PUBLICATIONS

Chinese Office Action received in corresponding Chinese Application No. 201380004874.8 dated Nov. 15, 2016.

* cited by examiner

DICTIONARY TABLE

| Name | Category |
|---|---|
| cirrhosis of liver | disease name |
| hepatocellular carcinoma | disease name |
| TAE | operative procedure |
| survival rate | index |
| recurrence rate | index |
| size | amount |
| cm | unit |
| not more than | magnitude |

Radiology. 1993 Jul; 188(1):79-83.
Taro Kimura and Jiro Suzuki
ABSTRACT   803
We have retrospectively analyzed effect of <u>TAE therapy</u> for <u>small hepatocellular carcinoma</u> with <u>cirrhosis of liver</u> using <u>Lipiodol</u>. The size of <u>hepatocellular carcinoma</u> is not more than 4 cm. The <u>recurrence rate</u>s of one year and four years are respectively 18% and 33%. The <u>survival rate</u>s of one year and four years are respectively 100% and 67%. TAE therapy is effective for small hepatocellular carcinoma.

804

KEYWORD
hepatocellular carcinoma
cirrhosis of liver
retrospective study

LITERATURE RANK TABLE

FIG. 10

| Clinical Study Type ||
|---|---|
| Level | Content |
| 1a | Meta-analysis of randomized comparison test |
| 1b | At least one randomized comparison test |
| 2a | Concurrent control cohort study without random allocation (forward-looking study, prospective study, concurrent cohort study, and the like) |
| 2b | Past control cohort study without random allocation (historical cohort study, retrospective cohort study, and the like) |
| 3 | Case control study (retrospective study) |
| 4 | Before/after comparison such as comparison before and after treatment without group to be compared |
| 5 | Case report, case series |
| 6 | Opinion of individual expert (including report of expert committee) |

FIG. 11

MEDICAL KNOWLEDGE MANAGING TABLE

| Knowledge No. | Literature No. | Word 1 | Word 2 | Co-Occurrence Degree | Literature Rank | Type |
|---|---|---|---|---|---|---|
| 1 | 1 | hepatocellular carcinoma | cirrhosis of liver | 3 | 4 | disease name |
| 2 | 4 | hepatocellular carcinoma | Lipiodol | 4 | 4 | amount/time-related information |
| ... | ... | ... | ... | ... | ... | ... |

FIG. 13

PATIENT TABLE

| Patient Code | Sex | Age | Disease Name | Date Of Admission | Date Of Discharge | Date Of Outpatient |
|---|---|---|---|---|---|---|
| P0 | Male | 60 | myocardial infarction | 1/1 | 2/1 | - |
| P1 | Female | 70 | hepatoma | 1/11 | 2/1 | - |
| P2 | Male | 80 | hepatoma | 1/21 | 2/1 | - |
| P3 | Male | 60 | hepatoma | - | - | 4/1 |
| P4 | Female | 70 | hepatoma | 11/1 | 12/1 | - |
| P5 | Male | 80 | hepatoma | - | - | 5/1 |
| P6 | Male | 50 | hepatoma | 11/11 | 12/1 | - |
| ... | ... | ... | ... | ... | ... | ... |

CLINICAL INDEX TABLE

| Patient Code | Date Of Admission | Date Of Discharge | Date Of Outpatient | Length Of Stay | Readmission |
|---|---|---|---|---|---|
| P0 | 1/1 | 2/1 | - | 31 | 0 |
| P1 | 1/11 | 2/1 | - | 21 | 1 |
| P2 | 1/21 | 2/1 | - | 11 | 0 |
| P3 | - | - | 4/1 | - | 0 |
| P4 | 11/1 | 12/1 | - | 31 | 0 |
| P5 | - | - | 5/1 | - | 0 |
| P6 | 11/11 | 12/1 | - | 21 | 0 |
| ... | ... | ... | ... | ... | ... |

FIG. 14

TREATMENT RECORD TABLE

| Patient Code | Diagnostic Process | Unit Cost | Date Of Treatment | Elapsed Day(s) | Care Provider |
|---|---|---|---|---|---|
| P0 | Artery marking | 300 | 1/1 | 1 | A1 |
| P0 | Sigmart | 200 | 1/1 | 1 | A2 |
| P1 | Lipiodol | 5000 | 1/12 | 2 | A2 |
| ... | ... | | ... | ... | ... |

DIAGNOSTIC PROCESS ANALYSIS SYSTEM

TECHNICAL FIELD

The present invention relates to a technique of a hospital information system in medical field and particularly relates to a diagnostic process analysis system.

BACKGROUND ART

Recently, an environment surrounding medical treatment has largely changed due to declining birthrate and an aging society, and progress in medical technology, for example. In particular, medical care expenditure in the world has increased by 5% a year both in developed countries and developing countries due to super-aging society starting from developed countries, causing an urgent issue of suppressing medical care expenditure while maintaining Quality of Life (QoL). It is particularly important to analyze and provide an optimal diagnostic process. What is especially desired upon evaluation of a "value (effect)" of a diagnostic process is to evaluate the value of a diagnostic process not based on a simple cost but on a cost required for the all processes of a patient who was in the diagnostic process through a follow-up survey.

PTL 1 provides a system that evaluates medical efficiency based on a master table in which positions of a user and physical condition evaluation indices are associated, action history of the user, and taken medicine (detected by detecting that a package is opened).

CITATION LIST

Patent Literature

PTL 1: JP 2011-243140 A

SUMMARY OF INVENTION

Technical Problem

Upon evaluation of cost required for the all processes, it is difficult to eliminate processes that are not relevant to a target diagnostic process because many patients have various comorbidities. For example, upon analyzing hepatoma of a patient with myocardial infarction as a comorbidity, there is a demand of easily eliminating processes for myocardial infarction. However, for elimination, all diagnostic processes have to be checked, and medical knowledge is also required, thus requiring a lot of labor.

In addition, upon evaluation of a target diagnostic process, what is required is not discussion of simple means of all patterns but discussion of each clinically meaningful homogeneous group of combination of processes because cost and quality largely depends on a combination of diagnostic processes (diagnostic process pattern). However, clustering of clinically homogeneous patients is difficult because many patients are in many diagnostic processes.

The system of above-described PTL 1 evaluates medical efficiency based on physical condition evaluation indices according to a behavior pattern of a user (ex. go to an amusement park, go to a hospital) without taking account of diagnostic process patterns.

As described above, according to the conventionally disclosed technique, it has been difficult to achieve enough effect on evaluating cost required for all processes.

Solution to Problem

Provided is a diagnostic process analysis system that analyzes cost-effectiveness of a diagnostic process by using a database storing clinical data, medical concept information indicating medical concepts, and text data, the system comprising: an input unit; an output unit; and a processing unit, wherein the input unit accepts input of a first diagnostic process to be analyzed, the processing unit includes: a medical knowledge extraction unit configured to extract, from the text data, relevance information indicating relevance between different medical concepts regarding the medical concept information of respective data pieces of the clinical data that are previously defined; an important process calculation unit configured to calculate importance scores of the data pieces of the clinical data by using the relevance information; a relevant process extraction unit configured to extract a second diagnostic process by eliminating diagnostic processes that are less relevant to the first diagnostic process, which has been accepted by the input unit, based on the importance scores; a patient clustering unit configured to perform clustering on patients in the clinical data based on the second diagnostic process and the importance scores calculated by the important process calculation unit; and an evaluation index calculation unit configured to calculate a clinical index and a cost of the second diagnostic process for each patient group obtained by clustering performed by the patient clustering unit, and the output unit outputs a result of calculation performed by the evaluation index calculation unit.

Advantageous Effects of Invention

The invention allows extraction of diagnostic processes that are not relevant to a target diagnostic process (administration of medicine, for example), thereby allowing calculation of total cost and a clinical index of processes caused by the target diagnostic process. In addition, upon evaluation of a diagnostic process, clinically homogeneous groups are generated so as to allow extraction of diagnostic process patterns (combinations) having bad clinical indices. Furthermore, since a diagnostic process is evaluated using clinically homogeneous groups, the diagnostic processes can be easily improved.

BRIEF DESCRIPTION OF DRAWINGS

FIG. 8 is an example of a medical literature processed by the diagnostic process analysis system according to the present inventions.

FIG. 10 is an example of evidence levels processed by the diagnostic process analysis system according to the present invention.

FIG. 11 is an output example of a medical knowledge output unit of the diagnostic process analysis system according to the present invention.

FIG. 13 is examples of a patient table and a clinical index table of the diagnostic process analysis system according to the present invention.

FIG. 14 is a treatment record table example of the diagnostic process analysis system according to the present invention.

DESCRIPTION OF EMBODIMENTS

First Embodiment

Figure 1:
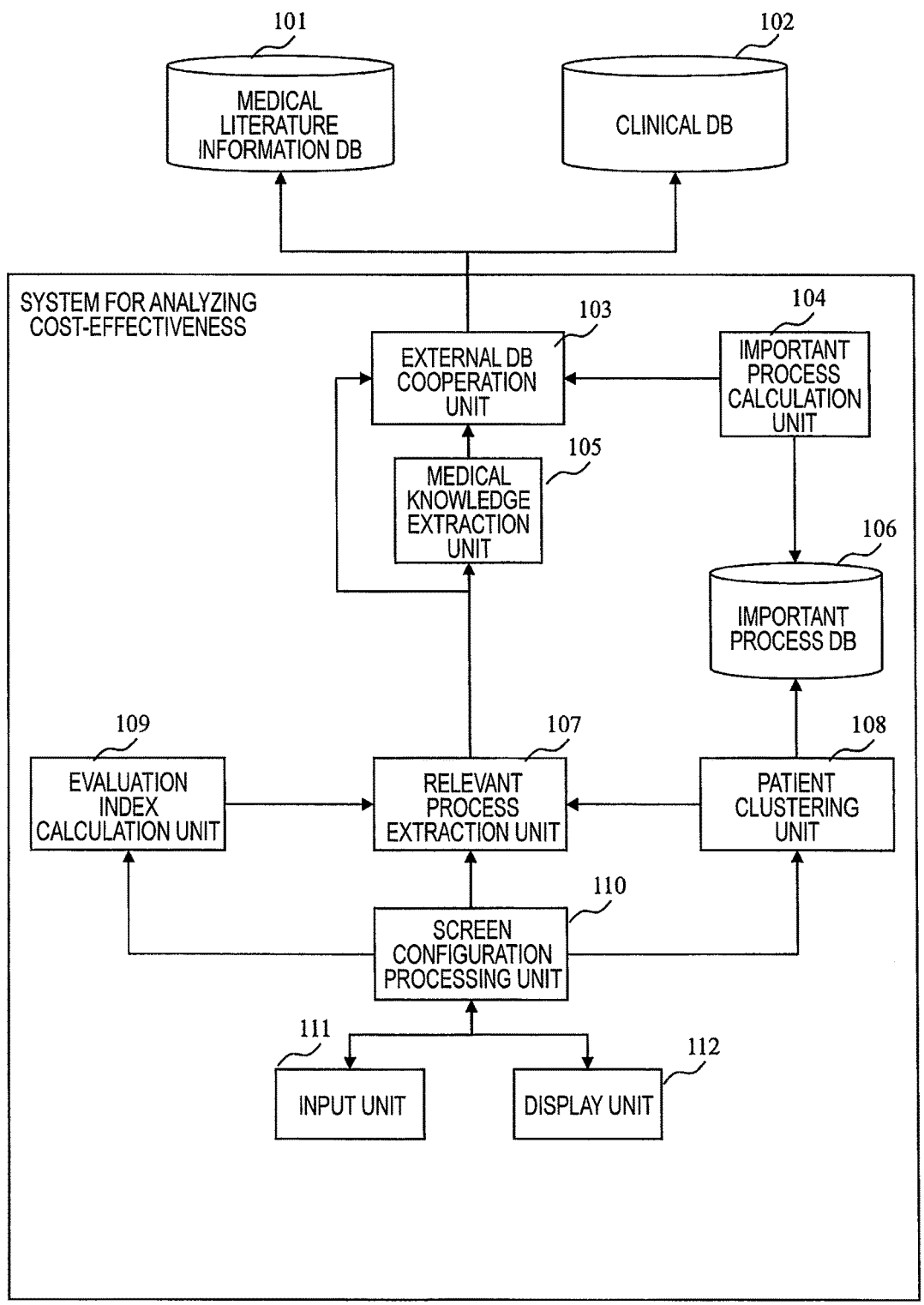
FIG. 1 is a schematic block diagram of a diagnostic process analysis system according to the present invention.

FIG. 1 is a block diagram of a diagnostic process analysis system according to the present invention. The system includes an external DB cooperation unit 103; an important process calculation unit 104; a medical knowledge extraction unit 105; an important process database 106; a relevant process extraction unit 107; a patient clustering unit 108; an evaluation index calculation unit 109; a screen configuration processing unit 110; an input unit 111; and a display unit 112. The external DB cooperation unit 103 is a function for cooperating with a database outside of the system. In the present embodiment, data stored in a medical literature information database 101 and a clinical database 102 are acquired via the external DB cooperation unit 103. The external DB cooperation unit 103 may cooperate with other databases in some embodiments.

Figure 2:
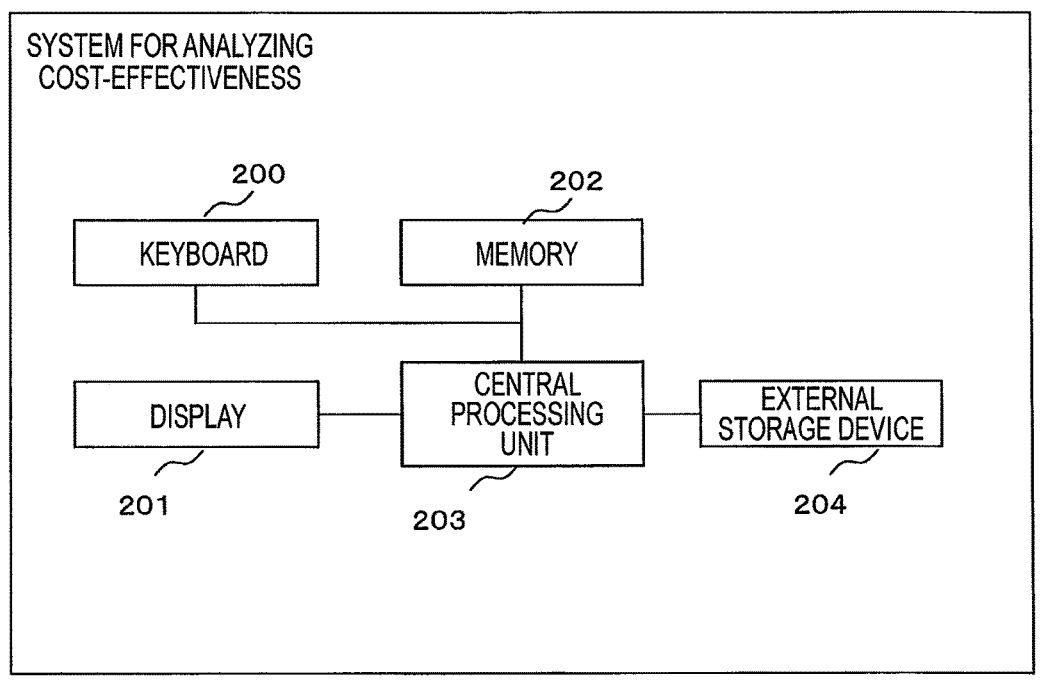
FIG. 2 is a hardware block diagram of the diagnostic process analysis system according to the present invention.

The hardware configuration of the system is described. FIG. 2 illustrates a hardware block diagram for implementing the diagnostic process analysis system according to the present invention. The important process database 106 is formed in an external storage device 204 or the like. The external storage is exemplified by a Hard Disk Drive (HDD) device. The external DB cooperation unit 103, the important process calculation unit 104, the medical knowledge extraction unit 105, the relevant process extraction unit 107, the patient clustering unit 108, the evaluation index calculation unit 109, and the screen configuration processing unit 110 can implement various types of processing by loading and executing a predetermined program by a central processing unit 203, a memory 202, or the like. The input unit 111 can be implemented by a keyboard 200, a mouse, a pen tablet, or the like. The display unit 112 can be implemented by a display 201 such as a liquid crystal display, a monitor of Cathode-Ray Tube (CRT) or the like. Information may be output on a medium such as paper.

Figure 3:
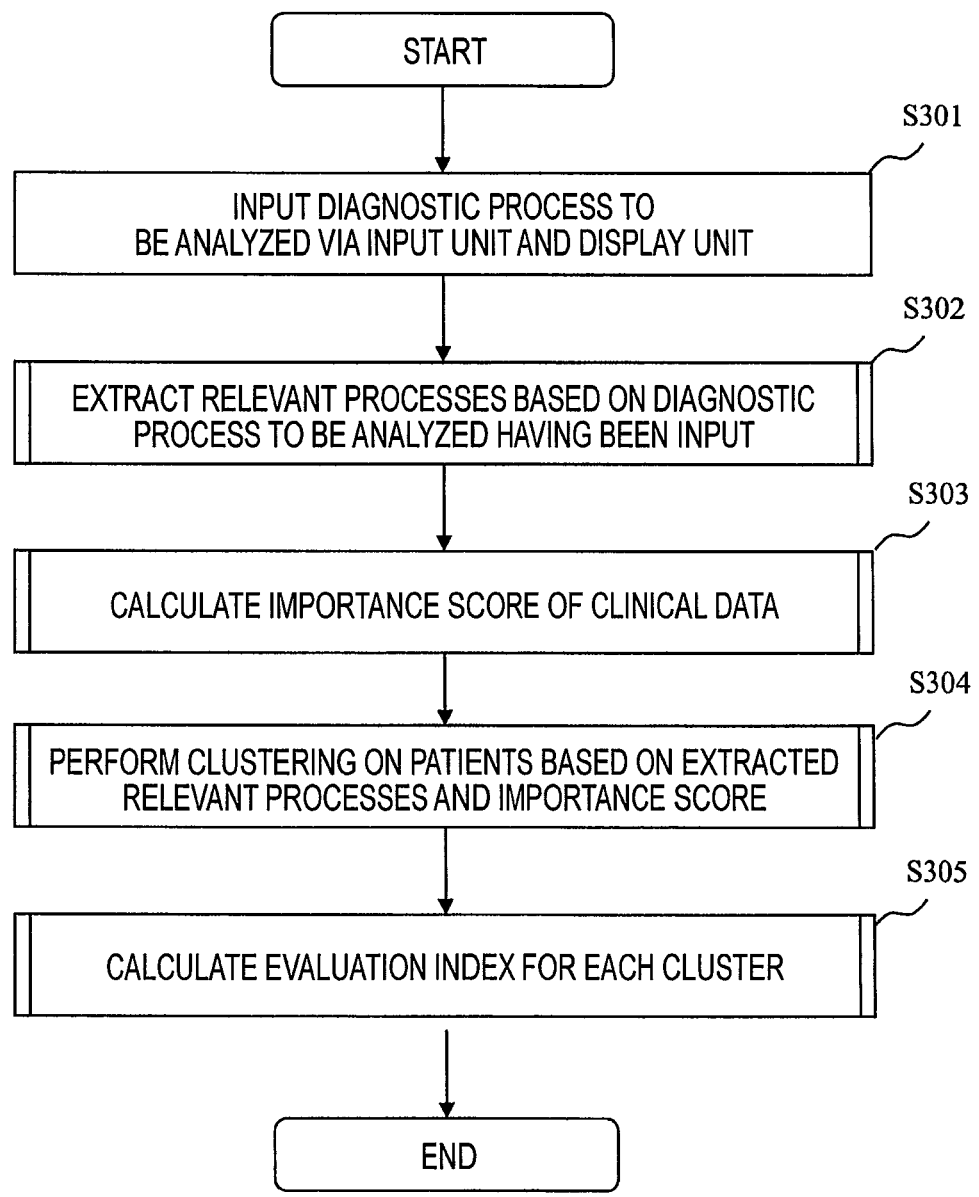
FIG. 3 is a first flowchart showing a process flow of the diagnostic process analysis system according to the present invention.

FIG. 3 illustrates a flowchart schematically showing the system. First, a diagnostic process to be analyzed is input via the input unit 111 and the display unit 112 (S301). Next, based on the diagnostic process to be analyzed having been input in S301, diagnostic processes that are relevant to the diagnostic process to be analyzed are extracted (S302). Next, importance scores of data pieces of clinical data are calculated by using data stored in the clinical database 102 (S303). Next, based on the relevant processes extracted in S302 and the importance scores calculated in S303, clustering is performed on patients (S304). Last, for each of clusters given by clustering in S304, an evaluation index (also referred to as a clinical indicator and a quality indicator) is calculated (S305). Note that S303 may be performed at any time before S304 and thus can be performed before these steps in advance.

Figure 4:
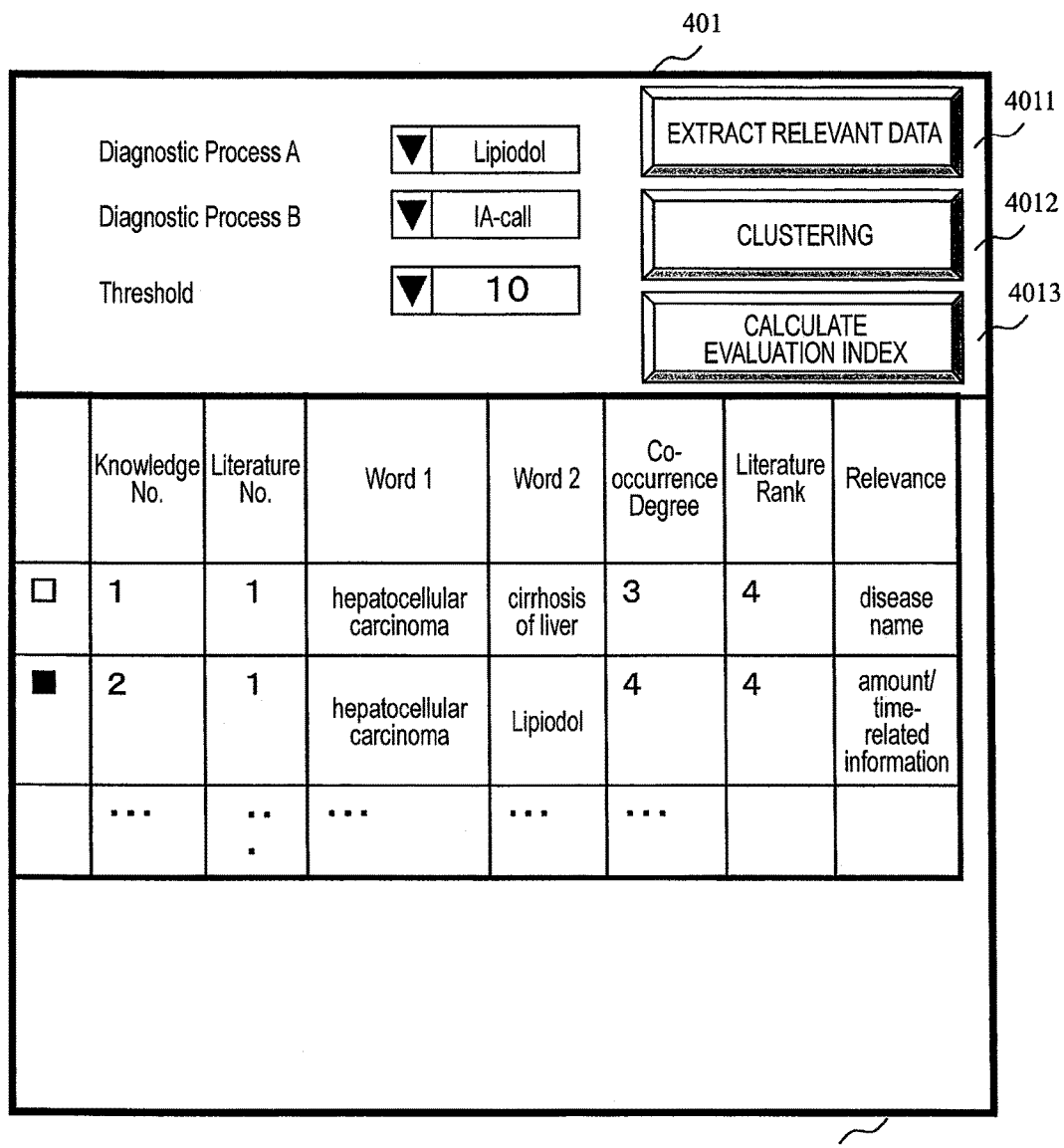
FIG. 4 is a first example illustrating a screen of the diagnostic process analysis system according to the present invention.

FIG. 4 illustrates a screen example that is displayed on the display unit 112 in S301 and S302. In this paragraph, only a part relating to S301 is described. This screen includes a condition setting part 401 and a processing result presenting part 402. In the condition setting part 401, there are displayed buttons for running a processing unit of the present system (a relevant data extraction button 4011, a clustering button 4012, and an evaluation index calculate button 4013) and various conditions. FIG. 4 illustrates the screen example of S301. Pressing the relevant data extraction button 4011 starts S302, pressing the clustering button 4012 starts S304, and pressing the evaluation index calculate button 4013 starts S305. In the condition setting part 401 of FIG. 4, conditions required to press the relevant data extraction button 4011 are displayed. In this example, Lipiodol and IA-call are set as diagnostic processes (medicines) to be analyzed. These diagnostic processes are used as anticancer drugs for hepatoma treatment. A user will analyze cost-effectiveness of the diagnostic processes. In the processing result presenting part 402, there is displayed a result after performing S302 by pressing the relevant data extraction button 4011.

Figure 5:
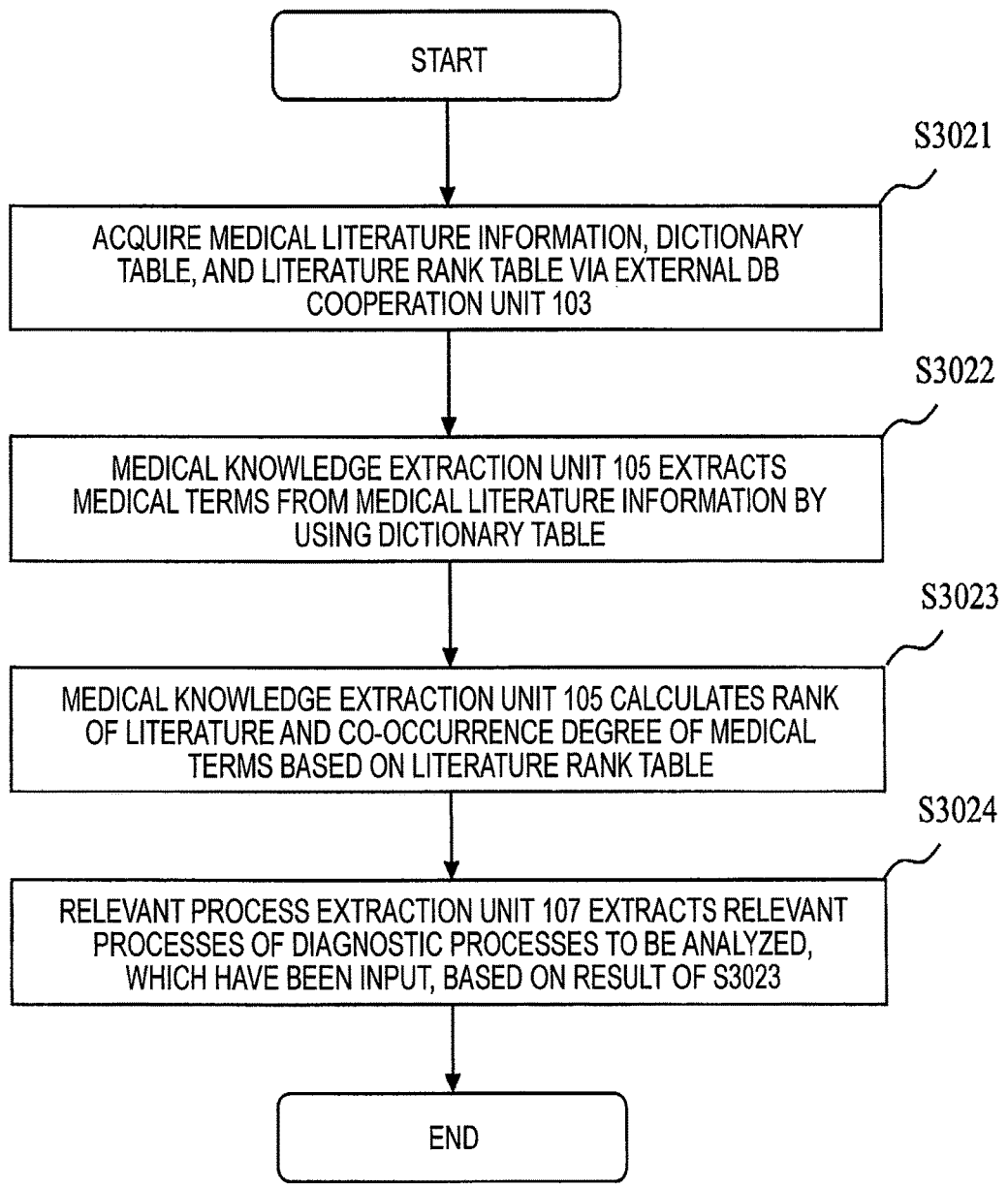
FIG. 5 is a flowchart showing a process flow of a relevant process extraction unit of the diagnostic process analysis system according to the present invention.

A detailed flowchart of S302 is provided in FIG. 5. First, the relevant process extraction unit 107 extracts medical knowledge via the medical knowledge extraction unit 105 (S3021 to S3023) and then extracts relevant processes (S3024). The detail is as follows.

Figure 7:
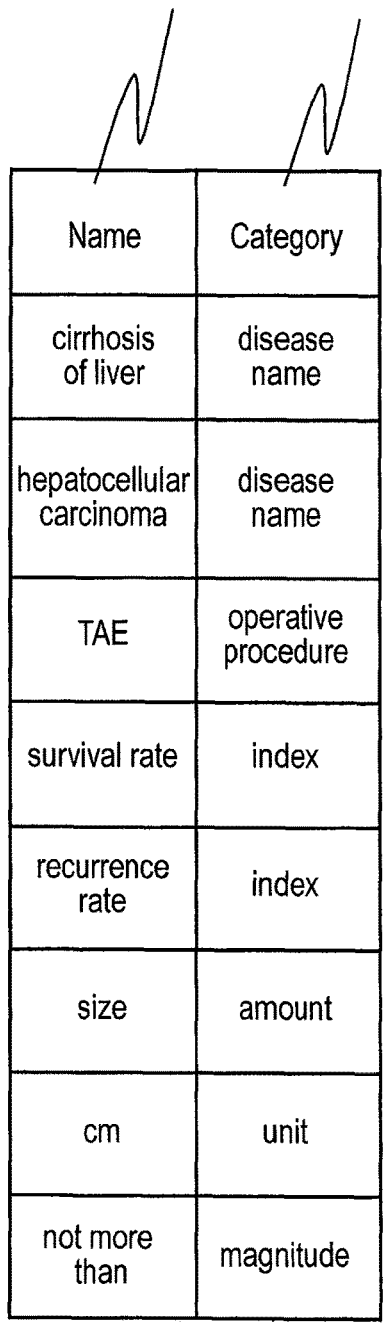
FIG. 7 is an example of a dictionary table that is processed by the diagnostic process analysis system according to the present invention.
Figure 9:
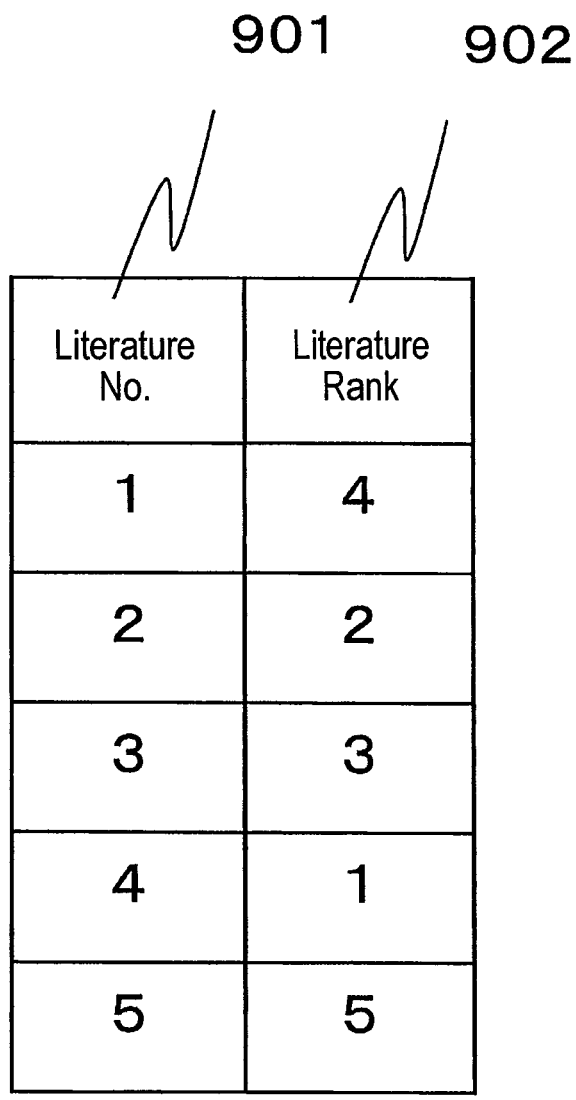
FIG. 9 is an example of a literature rank table processed by the diagnostic process analysis system according to the present invention.

First, the medical knowledge extraction unit 105 acquires medical literature information and a dictionary table from the medical literature information database 101 via the external DB cooperation unit 103 (S3021). FIG. 7 illustrates a dictionary table. The dictionary table is used to extract medical concepts from medical literatures and includes fields of name 701 and category 702. In the field of name 701, words of medical concepts that have been extracted from medical literatures are recorded. In the field of category 702, categories of the words are recorded. The categories include disease name, operative procedure name, index name, and pharmaceutical name. FIG. 9 is a table in which ranks of the respective literatures are recorded and which includes a field of literature number 901 and a field of literature rank 902. In the present embodiment, clinical study levels of FIG. 10 are used as the literature ranks. The clinical study levels indicate reliabilities of studies or strength as evidence of respective studies.

Figure 6:
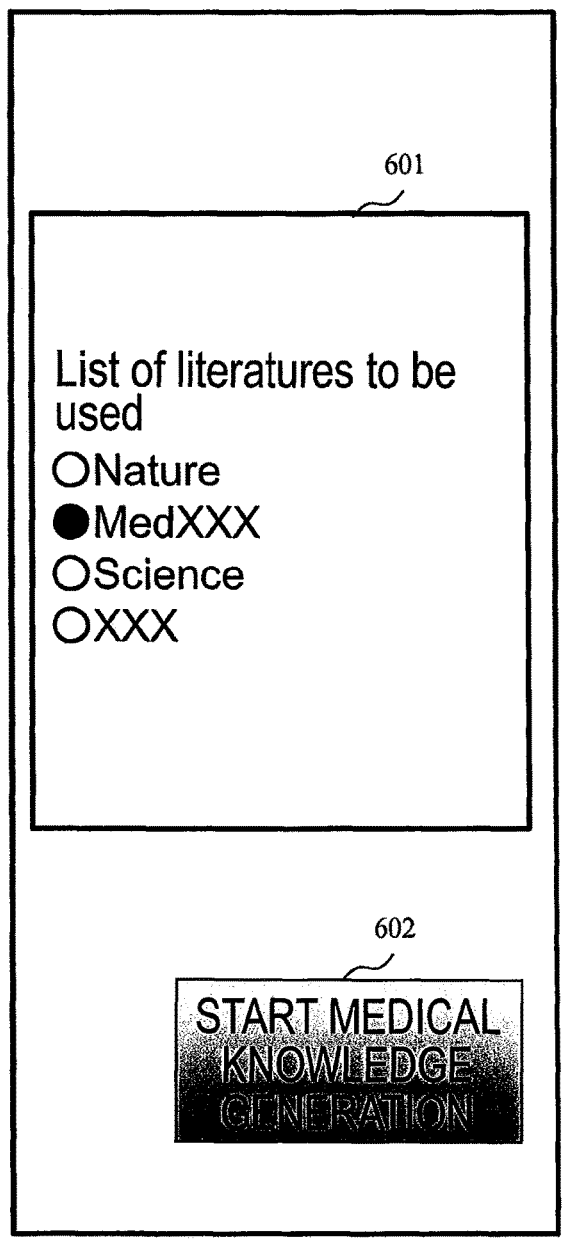
FIG. 6 is a screen example relating to the relevant process extraction unit of the diagnostic process analysis system according to the present invention.

FIG. 6 is a screen example used in the present embodiment. This is a screen used in S3021. A literature DB specifying part 601 is an area for specifying a literature DB to be processed by the program out of medical literatures stored in the medical literature information DB 101. A medical knowledge generation start button 602 is a button to start the process of the program. When the medical knowledge generation start button 602 is clicked, the medical knowledge extraction unit 105 acquires a medical literature specified in the literature DB specifying part 601 from the medical literature information DB 101. FIG. 8 is an example of a medical literature. The information includes a literature title 801, a date of publish 802, an abstract 803, and keywords 804. The medical knowledge extraction unit 105 similarly acquires the dictionary table illustrated in FIG. 7 and the literature rank table from the medical literature information DB 101.

Next, the medical knowledge extraction unit 105 extracts medical terms from the abstract of the medical literature based on the field of name 701 of each record having disease name, operative procedure, or index in the field of category 702 in the dictionary table (S3022). Underlined parts in the abstract 803 of FIG. 8 are medical terms extracted based on the dictionary table of FIG. 7. Next, the medical knowledge extraction unit 105 calculates an identification of the rank of the literature and co-occurrence degree of medical terms and amount/time-related information extracted in S3022 based on keywords of the literature information (S3023). Here, a co-occurrence degree of item A and item B is defined as the number of literatures that include both of item A and item B. In S3023, the medical knowledge extraction unit 105 registers the co-occurrence degree and the resultant rank to a medical knowledge managing table of FIG. 11 on a memory. Last, the relevant process extraction unit 107 extracts relevant processes of the diagnostic processes to be analyzed, which have been input, based on the result of S3023 (the co-occurrence degrees and the literature ranks in the medical knowledge managing table) (S3024). For example, the relevant process extraction unit 107 extracts, from records in the medical knowledge managing table, records having word 1 (or word 2) that matches the diagnostic processes to be analyzed, which have been input, and then narrows down the records to extract records having a co-occurrence degree and a literature rank that are higher in the medical knowledge managing table. Thus, importance scores are calculated using levels of academic literatures as evidence and co-occurrence degrees of respective terms, enabling to acquire knowledge of the academic literature and set importance scores corresponding to reliabilities of the studies. Therefore, process analysis by clustering diagnostic processes using results of medical academic studies in progress day by day corresponding to their evidence.

As a method of narrowing down records having a co-occurrence degree and a literature rank that are higher in the medical knowledge managing table, in the present embodiment, the condition setting part 401 of FIG. 4 is designed to allow setting of an integrated value of a co-occurrence degree and a literature rank as a threshold. In addition, in FIG. 4, the medical knowledge managing table is displayed in the processing result presenting part 402 so as to allow a user to select a relevant process. In the present embodiment, a state where a combination of hepatocellular carcinoma and lipiodol is selected is illustrated. In the present embodiment, a user selects a relevant process, but a user may select a non-relevant process using the threshold and the like in the condition setting part 401. Through such control of the threshold by a user, relevance between processes can be controlled to extract diagnostic processes responding to various needs, whereby various types of analysis of diagnostic processes are possible.

Figure 12:
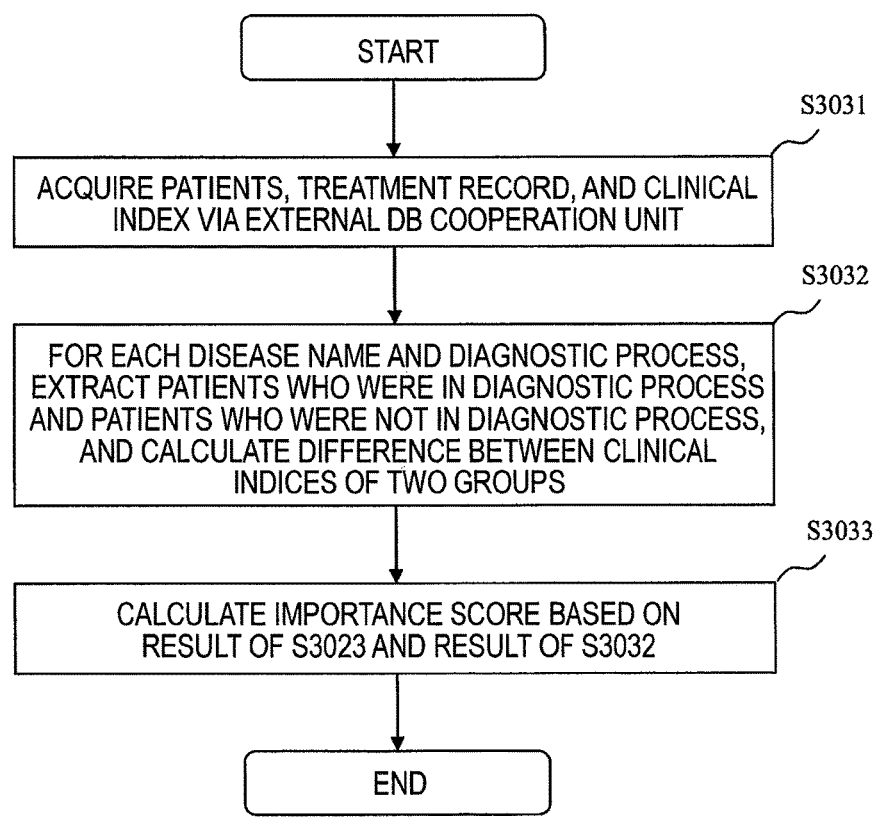
FIG. 12 is a flowchart showing a process flow of an important process calculation unit of the diagnostic process analysis system according to the present invention.

A detailed flowchart of S303 is provided in FIG. 12. First, a patient table, a clinical index table, and a treatment record table stored in the clinical DB 102 are acquired via the external DB cooperation unit 103 (S3031). FIG. 13 provides an example of the patient table and the clinical index table, and FIG. 14 provides an example of the treatment record table. The patient table includes patient code, sex, age, disease name, and information of date of admission/discharge (date of outpatient for an outpatient). The clinical index table manages clinical index (also referred to as Clinical Indicator and Quality Indicator) and includes information of length of stay and hospital readmission in the present embodiment. The treatment record table manages diagnostic processes and indicates a state where lipiodol is administered to patient P1 in the present embodiment. Next, for each disease name and diagnostic process, patients who were in the diagnostic process and patients who were not in the diagnostic process are respectively extracted and a difference between clinical indices of the two groups is calculated (S3032). In the present embodiment, a group of patient P1 who is a hepatoma patient and who was in the diagnostic process of lipiodol and a group of patients P2 to P6 who are hepatoma patients but who were not in the diagnostic process of lipiodol are extracted, and a difference between clinical indices of the two groups is calculated. As a calculation method, a difference of means of the clinical indices of the two groups may be calculated, or result of test for the difference of means of the clinical indices of the two groups may be calculated. Last, based on the result of S3023 and the result of S3032, an importance score is calculated for each disease name/diagnostic process (S3033). When an importance score is calculated based only on the result of S3023, an integrated value of a co-occurrence degree and a literature rank of the medical knowledge managing table is set as the importance score similarly to S3024. When an importance score is calculated based only on the result of S3032, the difference between clinical indices of the two groups calculated in S3032 is set as the importance score. When an importance score is calculated based on both of the results of S3023 and S3032, the sum or an integrated value of the both results is set as the importance score. Thus, processes that are highly important regarding to a clinical index in accordance with analysis needs are extracted, thereby enabling various types of analysis of diagnostic processes.

Figure 15:
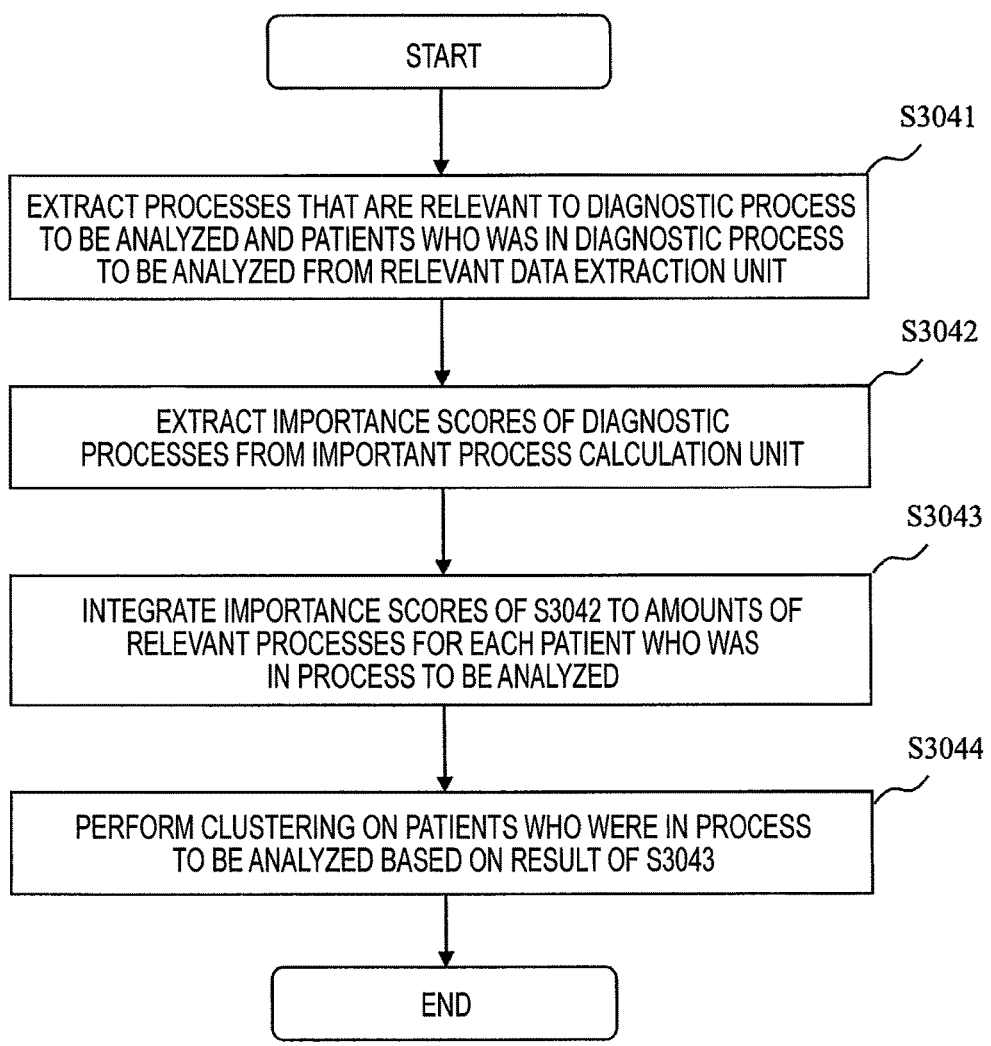
FIG. 15 is a flowchart showing a process flow of a patient clustering unit of the diagnostic process analysis system according to the present invention.

A detailed flowchart of S304 is provided in FIG. 15. The characteristic of this process is clustering of clinically similar patients based on clinically important diagnostic process. The clinically important diagnostic process means a diagnostic process that has an important influence on an outcome such as a death rate. For example, there is considered a method in which deterioration of clinical data is previously classified by degrees of deterioration, and an importance score is calculated based on the degrees. Thus, analysis of a diagnostic process in accordance with various types of analysis needs is possible by controlling a calculation method of an importance score.

In addition, a relevant data extraction unit 107 eliminates diagnostic processes that are less clinically-relevant, enabling to improve clustering accuracy and extract relevant processes using clinically divided groups.

Next, detailed flow is described. First, processes that are relevant to a diagnostic process to be analyzed and patients who was in the diagnostic process to be analyzed are extracted from the relevant data extraction unit (S3041). Next, importance scores of the diagnostic processes are extracted from the important process calculation unit (S3042). Next, the importance scores of S3042 are integrated to amounts of the relevant processes for each patient who was in the process to be analyzed (S3043). Last, clustering is performed on the patients who were in the process to be analyzed based on the integrated amounts that are result of S3043 (S3044).

Figure 16:
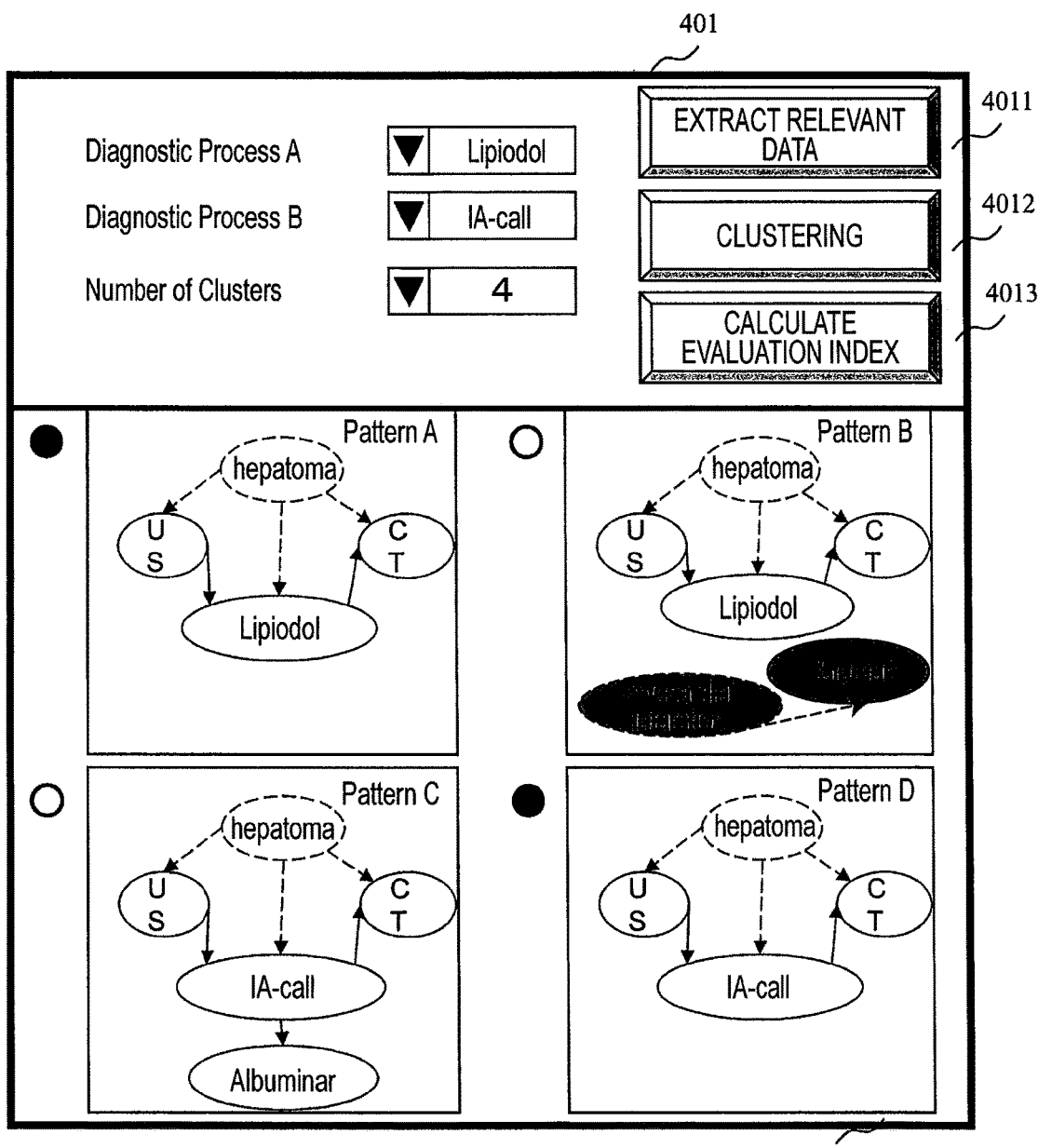
FIG. 16 is a screen example that is related to the patient clustering unit of the diagnostic process analysis system according to the present invention.

Here, FIG. 16 provides a screen example in which result of calculation of importance scores and clustering in S303 and S304 are displayed on the display unit 112. Pressing the clustering button 4012 starts the processes of S303 and S304. In the condition setting part 401 of FIG. 16, conditions required to press the clustering button 4012 are displayed, and the number of clusters used in S304 is set. In the present embodiment, four is set as the number of clusters. In the processing result presenting part 402, a state where the patients are divided in four clusters (patterns A to D) as a result of S304 is provided. Since the number of clusters is thus accepted, clustering control is enabled. Therefore, scale of analysis regarding relevance of diagnostic processes can be adjusted, and the embodiment can meet various needs of diagnostic processes.

Note that, in the present embodiment, US and CT are displayed as diagnostic processes. These are displayed as diagnostic processes that have been determined to have higher importance scores in S303. Through the process of extracting diagnostic processes having higher importance scores, validity of clustering accuracy can be visually confirmed. In addition, in the present embodiment, a state where patterns A and D are selected and patterns B and C are not selected is provided. Pressing the evaluation index calculate button 4013 in this state enables display of evaluation indices of the selected patterns A and D.

Figure 17:
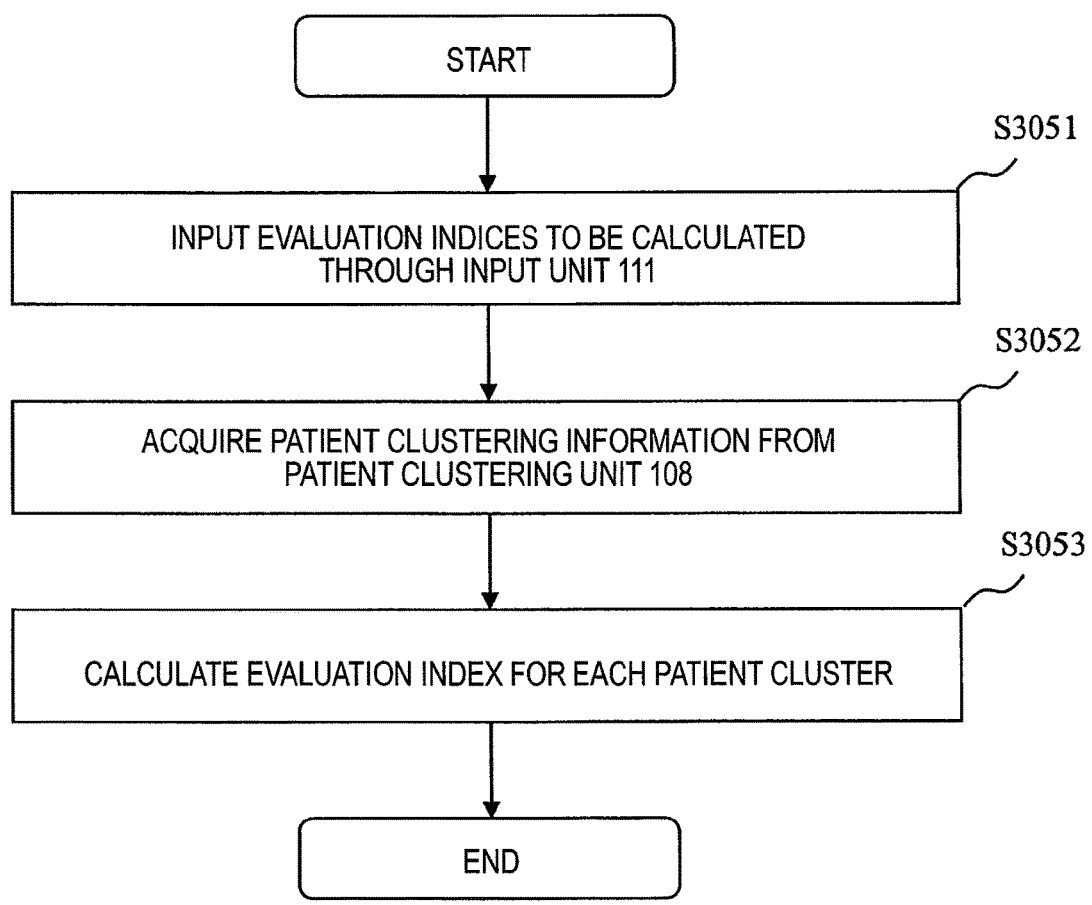
FIG. 17 is a flowchart showing a process flow of an evaluation index calculation unit of the diagnostic process analysis system according to the present invention.
Figure 18:
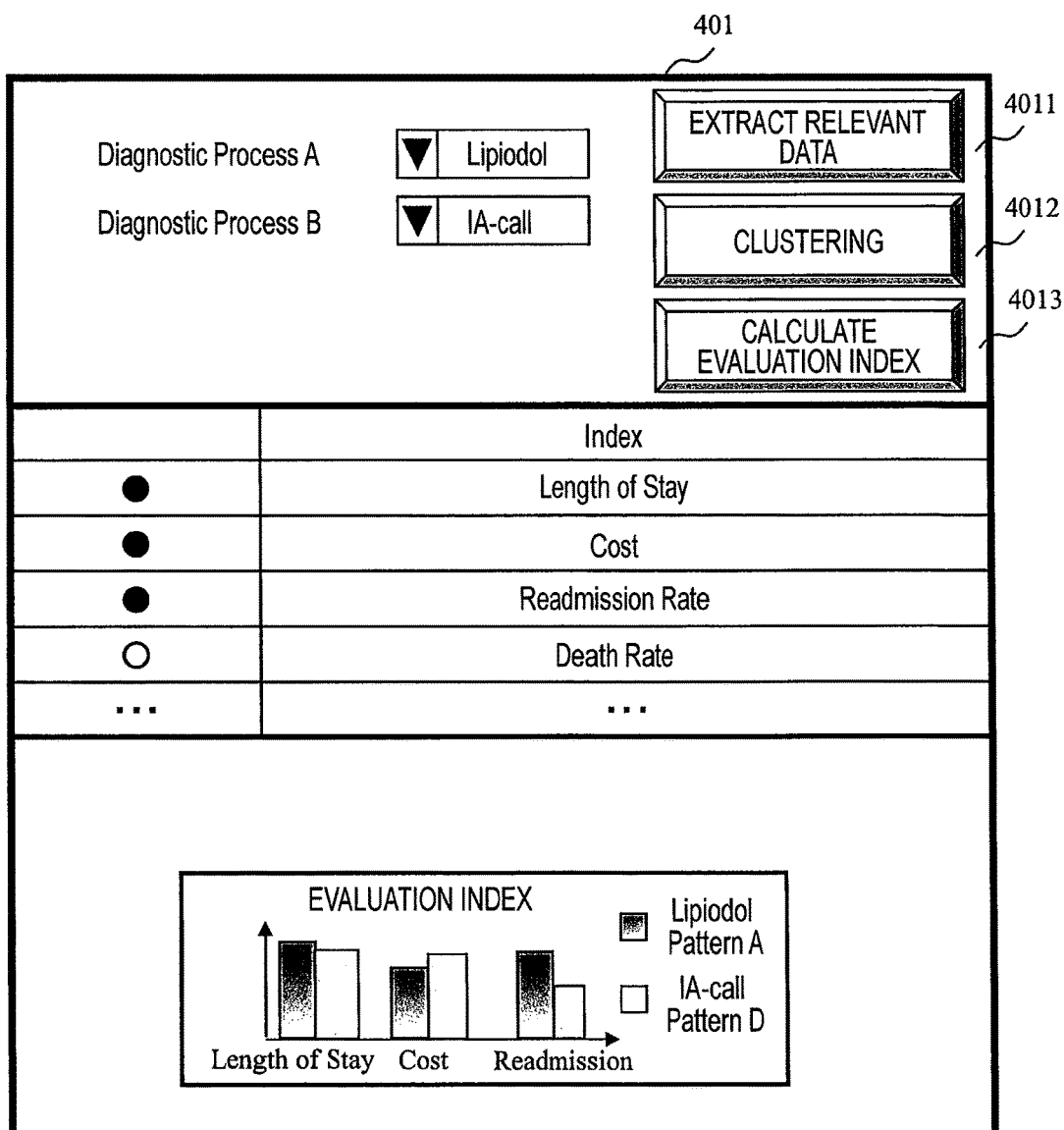
FIG. 18 is a screen example that is related to the evaluation index calculation unit of the diagnostic process analysis system according to the present invention.

Next, a detailed flowchart of S305 is provided in FIG. 17. First, through the input unit 111, evaluation indices to be calculated are input (S3051). FIG. 18 illustrates a screen example for displaying calculated importance scores and the result of clustering in S305 on the display unit 112. Pressing the evaluation index calculate button 4013 starts the process of S305. The condition setting part 401 of FIG. 16 is structured to allow selection of an evaluation index to be calculated. In the present embodiment, a length of stay, a cost, and a readmission rate are selected as evaluation indices to be calculated so as not to calculate a death rate.

Here, the description returns to the flowchart of FIG. 17. Next, patient clustering information is acquired from the patient clustering unit 108 (S3052). In the present embodiment, patients and diagnostic processes belonging to patterns A and D that have been selected in FIG. 16 are extracted. Last, an evaluation index is calculated for each patient cluster (S3053). In the present embodiment, means of lengths of hospital stay and readmission rates of patients of patterns A and D are respectively calculated and displayed in the processing result presenting part 402. Similarly, means of diagnostic process costs of respective patients in patterns A and D are respectively calculated based on the table of FIG. 14 and displayed as a cost in the processing result presenting part 402. The processing result presenting part 402 of FIG. 18 indicates a state where a cost of lipiodol is lower but a length of stay and a readmission rate thereof are higher. On the other hand, cost of IA-call is higher but a length of stay and a readmission rate thereof are lower. Thus, it can be seen that through the use of IA-call, lengths of hospital stay and readmission rates can be reduced, thereby suppressing a total cost.

According to the above-described system, upon evaluation of a "value (effect)" of a diagnostic process, the value of a diagnostic process can be evaluated not based on a simple cost but on a cost required for the all processes of a patient who was in the diagnostic process through a follow-up survey. In particular, upon evaluation of the value of the all processes, there exist many processes that are not clinically relevant to the diagnostic process to be analyzed. Thus, elimination of processes that are clearly different from the diagnostic process to be analyzed can improve evaluation accuracy of the value by a cost required for the all processes. Furthermore, the main object of evaluating the all processes is improvement. Therefore, upon value evaluation, each of combinations of processes, the combinations being clinically homogeneous as much as possible, is evaluated by using the present system, thereby allowing identifying a combination of processes to be improved.

INDUSTRIAL APPLICABILITY

The present invention relates to a hospital information system technique in medical field and is particularly useful as a technique that supports diagnostic process analysis.

REFERENCE SIGNS LIST 101 medical literature information database
102 clinical database
103 external DB cooperation unit
104 important process calculation unit
105 medical knowledge extraction unit
106 important process database
107 relevant process extraction unit
108 patient clustering unit
109 evaluation index calculation unit
110 screen configuration processing unit
111 input unit
112 display unit
200 keyboard
201 liquid crystal display
202 memory
203 central processing unit
204 external storage device
401 condition setting part
4011 relevant data extraction button
4012 clustering button
4013 evaluation index calculate button
402 processing result presenting part
601 literature DB specifying part
602 medical knowledge generation start button
701 name
702 category
801 literature title
802 date of publish
803 abstract
804 keyword
901 literature number
902 literature rank

The invention claimed is:
1. A diagnostic process analysis system that analyzes cost-effectiveness of a diagnostic process by using a database storing clinical data including patient information, medical concept information indicating medical concepts, and text data, the system comprising a computer programmed to:
accept input of a first diagnostic process, extract, from the text data, relevance information indicating relevance between different medical concepts regarding the medical concept information of respective data pieces of the clinical data that are previously defined;

calculate importance scores of the data pieces of the clinical data by using the relevance information indicating the relevance between different medical concepts regarding the medical concept information of respective data pieces of the clinical data that are previously defined;

extract a second diagnostic process having a relevance to the first diagnostic process, which has been accepted, higher than a predetermined threshold based on the importance scores;

perform clustering on the patient information of the clinical data based on the second diagnostic process and the calculated importance scores to generate patient groups; and calculate a clinical index and a cost of the second diagnostic process for each of the patient groups;

wherein the text is medical literatures;

wherein extracting the relevance information includes extracting evidence levels from study levels indicated by the medical literatures;

wherein calculating the importance scores includes calculating the importance scores of the data pieces of the clinical data based on the evidence levels and co-occurrence degrees between the medical concepts obtained by extracting the relevance information;

wherein a co-occurrence degree between a plurality of medical concepts is a number of medical literatures that each include all of the plurality of medical concepts;

wherein diagnostic processes that do not have relevance higher than the predetermined threshold based on the importance scores are eliminated from further consideration; and wherein one or more second diagnostic processes having relevance higher than the predetermined threshold are further considered by using the calculated clinical indices and costs of the one or more second diagnostic processes for the patient groups, combinations of diagnostic processes are evaluated, and a combination of diagnostic processes to be improved is identified.

2. The diagnostic process analysis system according to claim 1, wherein
calculating the importance scores includes evaluating deterioration degrees of the clinical index and calculating the importance scores further based on the evaluated deterioration degrees of the clinical index, the deterioration degrees classifying deterioration of the clinical data.

3. The diagnostic process analysis system according to claim 1, wherein the co-occurrence degree between the plurality of medical concepts is the number of medical literatures that each include all of a plurality of medical terms representing the plurality of medical concepts.

4. The diagnostic process analysis system according to claim 2, wherein
calculating the importance scores includes, for each of the diagnostic processes, extracting a group of patients who have been in the diagnostic process and a group of patients who have not been in the diagnostic process from the database, calculating a difference between the clinical indices of the two extracted groups, and evaluating the deterioration degree of the clinical index based on the calculated difference of the clinical indices.

5. The diagnostic process analysis system according to claim 1, wherein
performing clustering on the patient information of the clinical data includes accepting input of the number of clusters upon performing the clustering, and performing clustering on patients of the clinical data based on the accepted number of clusters.

6. The diagnostic process analysis system according to claim 4, wherein
the deterioration degree of the clinical index is evaluated based on the difference between the clinical indices of the two extracted groups, and the importance score is calculated based in part on the difference between the clinical indices of the two extracted groups.

7. The diagnostic process analysis system according to claim 4, wherein
calculating the importance scores includes, for each one of the diagnostic processes, calculating the importance score based on the evidence levels and co-occurrence degrees between the medical concepts obtained by extracting the relevance information for the data pieces of the clinical data that are relevant to said one of the diagnostic processes, and the evaluated deterioration degree of the clinical index.

8. The diagnostic process analysis system according to claim 7, wherein
the deterioration degree of the clinical index is evaluated based on the difference between the clinical indices of the two extracted groups, and the importance score is calculated based in part on the difference between the clinical indices of the two extracted groups.

9. The diagnostic process analysis system according to claim 8, wherein
the clinical index includes information of length of stay in hospital and hospital readmission.

10. The diagnostic process analysis system according to claim 7, wherein
the clinical index includes information of length of stay in hospital and hospital readmission.

11. The diagnostic process analysis system according to claim 6, wherein
the clinical index includes information of length of stay in hospital and hospital readmission.

12. The diagnostic process analysis system according to claim 4, wherein
the clinical index includes information of length of stay in hospital and hospital readmission.

13. The diagnostic process analysis system according to claim 2, wherein
the clinical index includes information of length of stay in hospital and hospital readmission.

14. The diagnostic process analysis system according to claim 1, wherein
the clinical index includes information of length of stay in hospital and hospital readmission.

15. The diagnostic process analysis system according to claim 3, wherein the plurality of medical terms representing the plurality of medical concepts are extracted from abstracts of the medical literatures.

16. The diagnostic process analysis system according to claim 1,
wherein the identified combination of diagnostic processes are improved.

17. A diagnostic process analysis method for analyzing cost-effectiveness of a diagnostic process by using a database storing clinical data including patient information, medical concept information indicating medical concepts, and text data, the method comprising:

accepting input of a first diagnostic process, extracting, from the text data, relevance information indicating relevance between different medical concepts regarding the medical concept information of respective data pieces of the clinical data that are previously defined;

calculating importance scores of the data pieces of the clinical data by using the relevance information indicating the relevance between different medical concepts regarding the medical concept information of respective data pieces of the clinical data that are previously defined;

extracting a second diagnostic process having a relevance to the first diagnostic process, which has been accepted, higher than a predetermined threshold based on the importance scores;

performing clustering on the patient information of the clinical data based on the second diagnostic process and the calculated importance scores to generate patient groups;

calculating a clinical index and a cost of the second diagnostic process for each of the patient groups;

wherein the text is medical literatures;

wherein the extracting includes extracting evidence levels from study levels indicated by the medical literatures;

wherein the importance scores of the data pieces of the clinical data are calculated based on the evidence levels and co-occurrence degrees between the medical concepts obtained by extracting the relevance information; and wherein a co-occurrence degree between a plurality of medical concepts is a number of medical literatures that each include all of the plurality of medical concepts;

eliminating from further consideration diagnostic processes that do not have relevance higher than the predetermined threshold based on the importance scores are eliminated from further consideration; and further considering one or more second diagnostic processes having relevance higher than the predetermined threshold by using the calculated clinical indices and costs of the one or more second diagnostic processes for the patient groups, evaluating combinations of diagnostic processes, and identifying a combination of diagnostic processes to be improved.

18. The diagnostic process analysis method according to claim 17, wherein the co-occurrence degree between the plurality of medical concepts is the number of medical literatures that each include all of a plurality of medical terms representing the plurality of medical concepts.

19. The diagnostic process analysis method according to claim 18, wherein the plurality of medical terms representing the plurality of medical concepts are extracted from abstracts of the medical literatures.

20. The diagnostic process analysis method according to claim 17, further comprising:

improving the identified combination of diagnostic processes.

* * * * *